United States Patent
Young et al.

(12) 
(10) Patent No.: US 7,067,704 B2
(45) Date of Patent: Jun. 27, 2006

(54) PROCESS FOR PURIFYING BISPHENOL-A

(75) Inventors: Thomas C. Young, Lake Jackson, TX (US); Damian M. Feord, Strasbourg (FR); Johann-Wilhelm Frey, Stade (DE)

(73) Assignee: Dow Global Technologies Inc., Midland, MI (US)

( * ) Notice: Subject to any disclaimer, the term of this patent is extended or adjusted under 35 U.S.C. 154(b) by 0 days.

(21) Appl. No.: 10/530,432

(22) PCT Filed: Nov. 12, 2003

(86) PCT No.: PCT/US03/35900

§ 371 (c)(1),
(2), (4) Date: Apr. 6, 2005

(87) PCT Pub. No.: WO2004/048430

PCT Pub. Date: Jun. 10, 2004

(65) Prior Publication Data

US 2006/0014986 A1    Jan. 19, 2006

(51) Int. Cl.
*C07C 37/84* (2006.01)

(52) U.S. Cl. ............ 568/724; 568/722; 568/723; 568/725; 568/727; 568/749; 568/750

(58) Field of Classification Search ........ 568/724, 568/722, 723, 725, 727, 749, 750
See application file for complete search history.

(56) References Cited

U.S. PATENT DOCUMENTS

| | | | |
|---|---|---|---|
| 3,326,986 A | 6/1967 | Dugan et al. |
| 4,141,924 A | 2/1979 | Sun |
| 4,375,567 A | 3/1983 | Faler |
| 4,461,915 A | 7/1984 | Mendiratta et al. |
| 4,533,764 A | 8/1985 | Chang et al. |
| 4,740,635 A | 4/1988 | Gomes de Matos et al. |
| 4,822,923 A | 4/1989 | Li |
| 4,825,010 A | 4/1989 | Li |
| 4,861,919 A | 8/1989 | Robbins et al. |
| 5,105,026 A | 4/1992 | Powell et al. |
| 5,512,700 A | 4/1996 | Patrascu et al. |

FOREIGN PATENT DOCUMENTS

| | | |
|---|---|---|
| EP | 0 400 171 B1 | 12/1990 |
| EP | 0 552 518 | 7/1993 |
| EP | 0 558 214 A1 | 9/1993 |
| EP | 0 630 878 | 12/1994 |

*Primary Examiner*—Elvis O. Price

(57) ABSTRACT

Bisphenol-A is purified in a process which comprises the following steps: a) cooling a liquid mixture comprising bisphenol-A and water in a bisphenol-A crystallizer to form bisphenol-A crystals in a liquid phase; b) separating the bisphenol-A crystals from the liquid phase; c) dividing at least a portion of the liquid phase into a bisphenol-rich organic phase and a water-rich phase; d) feeding phenol and at least a portion of the bisphenol-rich organic phase into a adduct crystallizer to form a crystalline adduct of phenol and bisphenol-A in a mother liquor, and e) separating the crystalline adduct from the mother liquor. Bisphenol-A of high purity at a high yield is obtained.

19 Claims, 2 Drawing Sheets

PROCESS FOR PURIFYING BISPHENOL-A

The present invention relates to a process for the purification bisphenol-A and to purified bisphenol-A.

"Bisphenol-A" or "p,p'-bisphenol-A" are well-known names for 2,2-bis(4-hydroxyphenyl)-propane which is a condensation product of phenol and acetone. Bisphenol-A is a product of high technical and commercial importance for the manufacturing of many commercial products, such as polycarbonates and epoxy resins. The world production of Bisphenol-A in 1999 was over 2 million metric tons per year and is still growing. High quality epoxy resins, and particularly polycarbonates, require bisphenol-A of high purity for use in their preparation.

Bisphenol-A is prepared according to various known processes by the condensation reaction of a acetone and a stoichiometric excess of phenol in the presence of a catalyst. These known processes produce bisphenol-A and certain impurities including isomers, analogs and homologues, such as 2-(2-hydroxyphenyl)-2-(4-hydroxyphenyl)propane (hereafter referred to as o,p'-bisphenol-A), 2,2,4-trimethyl-4-(4-hydroxyphenyl)chroman, trisphenol, polyphenol and unfavorably colored substances. In view of the high technical and commercial interest in providing highly pure bisphenol-A, much research effort has been spent on its purification.

According to one known method a mixture of bisphenol-A and water is prepared, the mixture is heated and subsequently cooled to re-crystallize bisphenol-A.

U.S. Pat. No. 3,326,986 discloses mixing crude bisphenol-A with water and heating the mixture to a temperature of 100° C. resulting in an aqueous phase and a liquid organic phase. The mixture is cooled slowly to crystallize bisphenol-A. Any isomeric diphenols or other organic impurities remaining in the crystals are removed by washing with a chlorinated solvent, such as chloroform, methylene chloride, ethylene dichloride, propylene dichloride or chlorobenzene.

U.S. Pat. No. 4,461,915 suggests mixing water-crystallized bisphenol-A in the presence of water with a water-immiscible organic solvent, such as toluene, agitating the mixture and forming three phases in the agitated mixture. The phase containing mainly the organic solvent is removed and purified bisphenol-A is recovered from the remaining two phases.

U.S. Pat. No. 4,740,635 discloses a process for crystallizing bisphenol-A wherein water is added to a mixture of a phenol-free mixture of bisphenol-A, 0.5 to 15 wt.-percent diphenol isomers and impurities. Water and the crude bisphenol-A mixture are heated to 95–105° C. at ambient-pressure to melt all the solid material. Then it is adiabatically cooled, while stirring, by reducing the pressure. The temperature is reduced to below 90° C. The crystallized bisphenol-A may be washed to further increase its purity. Unfortunately, the maximum purity of the crystallized bisphenol-A, even after several washing operations, does not exceed 99.2 percent.

U.S. Pat. No. 4,533,764 discloses a process for removing occluded organic solvent from bisphenol crystals. The crystals are placed in water which is maintained at a temperature of 100° C. or above to produce a molten water-bisphenol phase. The water-bisphenol phase separates from the excess water and the solvent occluded by the bisphenol crystals can diffuse into the water phase from where it can be flash distilled.

U.S. Pat. No. 4,141,924 discloses a process for purifying a crude crystalline aromatic compound, such as bisphenol-A, wherein a dispersion of the liquefied crude material in an aqueous liquid is formed by agitating the mixture at ambient pressure and at a temperature sufficient to melt the crude material. Agitation is then reduced to permit formation of three phases, a solid crystalline phase, an aqueous liquid phase and a mother liquor phase.

U.S. Pat. No. 5,512,700 discloses a process for the purification of a crude bisphenol which comprises the steps of (1) preparing a mixture of a crude bisphenol-A and water at a pressure above atmospheric and a temperature above 100° C., (2) crystallizing bisphenol-A at a pressure below atmospheric, (3) separating crystalline bisphenol from the mother liquor, (4) dividing at least a portion of the mother liquor into a bisphenol-rich organic phase and a water-rich phase, (5) preparing a mixture of the bisphenol-rich organic phase, water and optionally an additional amount of crude bisphenol at a pressure above atmospheric and a temperature of above 100° C., (6) cooling the mixture and crystallizing bisphenol and (7) separating crystalline bisphenol from the mother liquor.

Many of the processes described in the above-mentioned patents provide bisphenol-A of high quality. Unfortunately, the patents do not teach how to optimize the yield of the bisphenol-A while still obtaining a high quality. A high quality alone is not sufficient considering the fact that bisphenol-A is produced on very large scale. Accordingly, it is very important to achieve a high quality bisphenol-A while optimizing the yield of the purification process. Even a small percentage in yield increase would result in huge savings in raw materials or in material that has to be recycled.

Accordingly, it is still desirable to provide a new process for purifying crude bisphenol-A.

One aspect of the present invention is a process for purifying bisphenol-A which comprises the steps of
 a) cooling a liquid mixture comprising bisphenol-A and water in a bisphenol-A crystallizer to form bisphenol-A crystals in a liquid phase;
 b) separating the bisphenol-A crystals from the liquid phase;
 c) dividing at least a portion of the liquid phase into a bisphenol-rich organic phase and a water-rich phase;
 d) feeding phenol and at least a portion of the bisphenol-rich organic phase into an adduct crystallizer to form a crystalline adduct of phenol and bisphenol-A in a-mother liquor; and
 e) separating the crystalline adduct from the mother liquor.

Another aspect of the present invention is purified bisphenol-A which is producible according to the above-mentioned process.

Figure 1:
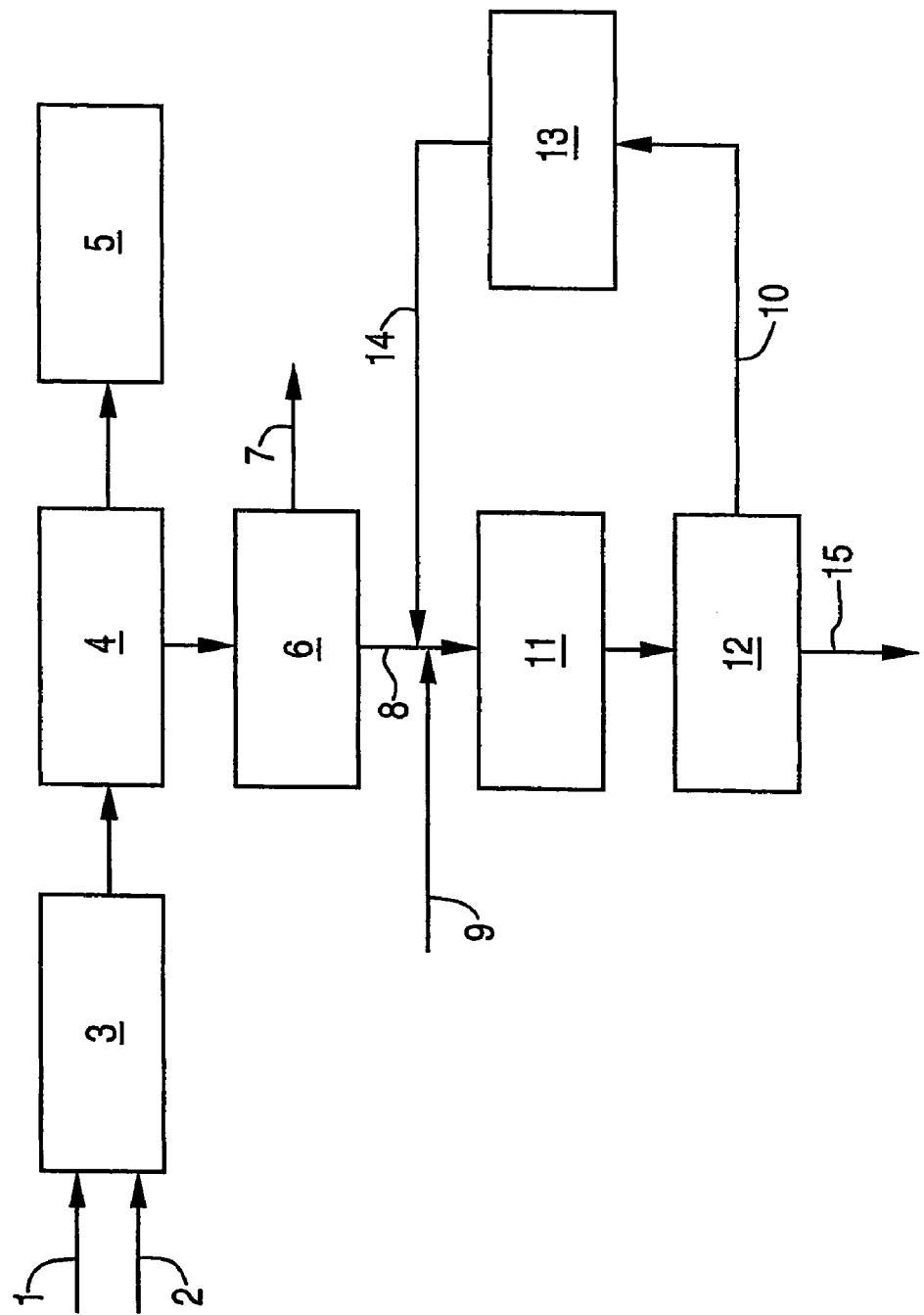
FIG. 1 represents a flow sheet of a preferred embodiment of the process of the present invention.

Preferably, the purity of the crude bisphenol-A which is purified according to the process of the present invention is 90 percent or more, more preferably 95 percent or more. The production of crude bisphenol-A of such purity is well known in the art. The impurities which may be removed by the purification process of the present invention include a variety of by-products of the bisphenol-A production, such as 2-(2-hydroxyphenyl)-2-(4-hydroxyphenyl)propane, also called o,p'-bisphenol-A; 2,2,4-trimethyl-4-(4-hydroxyphenyl)chroman, trishydroxyphenyl compounds, such as 4,4'-(4-hydroxy-m-phenylenediisopropylidene)diphenyl, polyphenols, isopropenylphenol and/or spiro biindanes.

The liquid mixture used in step a) of the process of the present invention preferably comprises from 20 to 80 percent, more preferably from 30 to 60 percent of crude bisphenol-A and preferably from 20 to 80 percent, more preferably from 40 to 70 percent of water, based on the total weight of the mixture. The term "a liquid mixture" means that the mixture is liquid at the conditions chosen in step a). The bisphenol can be preheated and partially or entirely molten before it is contacted with water. The bisphenol is preferably heated to a temperature of from 155 to 240° C., more preferably from 170 to 205° C. Water can also be preheated before it is contacted with bisphenol, preferably to a temperature of from 45 to 105° C., more preferably from 80 to 100° C. The mixture of bisphenol-A and water preferably is maintained at a pressure above 1 bar (100 kPa), preferably from 1.5 to 5 bar, and a temperature of from 105 to 150° C. In step a) of the process of the present invention the mixture is cooled in a bisphenol-A crystallizer to form bisphenol-A crystals in a liquid phase. Preferably the pressure is reduced to below atmospheric, more preferably to an absolute pressure of from 640 to 920 mbar (64 to 92 kPa). When lowering the pressure, the hot mixture of bisphenol-A and water is preferably cooled to a temperature of from 80 to 100° C., more preferably from 88 to 98° C. The cooling is preferably conducted adiabatically.

In step b) of the process of the present invention bisphenol-A crystals are separated from the liquid phase. Bisphenol-A crystals can be recovered by techniques known in the art, such as filtration or centrifugation, preferably at atmospheric pressure. The temperature in step b) generally is from 80 to 110° C., preferably from 92 to 105° C. The recovered crystals can be washed with an organic solvent or preferably with water. The washing liquor generally has a temperature of from 70 to 105° C., preferably from 85 to 100° C.

According to another preferred embodiment of the invention the bisphenol-A crystals which have been separated from the liquid phase in step b) are melted, mixed with water, cooled in a second bisphenol-A crystallizer to form bisphenol-A crystals in a liquid phase and the crystals are separated from the liquid phase. By this recrystallization step, wherein the bisphenol-A crystals obtained in step b) are melted and steps a) and b) are repeated, a further purification is achieved. This recrystallization process can be conducted one or more times.

In step c) of the process of the present invention at least a portion of the liquid phase is divided into a bisphenol-rich organic phase and a water-rich phase. Preferably at least 75 percent of the total volume and most preferably the entire volume of the liquid phase is separated into the two phases. The two phases can be separated by known means, such as decantation or centrifugation. The temperature in step c) generally is from 60 to 105° C., preferably from 75 to 95° C. The resulting water-rich phase generally contains more than 50 percent, preferably more than 70 percent of the total weight of water present in the liquid phase. The entire amount or a part of the water-rich phase can be disposed of or recycled to step a). The resulting bisphenol-rich organic phase generally contains more than 50 percent, preferably more than 80 percent of the total weight of bisphenol-A present in the liquid phase. At least a portion, preferably at least 50 percent, more preferably at least 60 percent of the bisphenol-rich phase is used in the subsequent step d) of the process of the present invention. Before using the bisphenol-rich phase in step d), it is optionally subjected to an additional treatment, for example a distillation to remove water that remains in the bisphenol-rich phase after decantation or centrifugation in step c).

If bisphenol-A crystals are recrystallized in a second bisphenol-A crystallizer, the liquid phase recovered from the second bisphenol-A crystallizer is preferably, also divided into a bisphenol-rich organic phase and a water-rich phase as described in step c) above. The bisphenol-rich organic phase may be either used in step d) as described below or, preferably, recycled for use in the initial step a).

In step d) of the process phenol and at least a portion of the bisphenol-rich organic phase are fed into a adduct crystallizer to form a crystalline adduct of phenol and bisphenol-A in a mother liquor. Fresh or recovered phenol or both can be used in step d). For example, phenol can be recovered by distilling off phenol from an adduct of phenol and bisphenol-A, preferably from an adduct of phenol and bisphenol-A that is obtained in step e) as described further below. According to another preferred embodiment of the present invention recycled phenol can be used in step d) that has been used for washing an adduct of phenol and bisphenol-A that is obtained in step e) as described further below. Preferably, at least a portion of a mother liquor that is obtained in step e) as described further below is also fed into an adduct crystallizer. The weight ratio between the bisphenol-rich organic phase, the phenol and optionally the mother liquor is preferably chosen such that the mixture in the adduct crystallizer comprises from 8 to 60 percent, more preferably from 12 to 40 percent, most preferably from 15 to 30 percent of bisphenol-A; from 25 to 85 percent, more preferably from 30 to 80 percent, most preferably from 40 to 75 percent of phenol; and optionally up to 20 percent, preferably up to 15 percent of other components, such as 2-(2-hydroxyphenyl)-2-(4-hydroxyphenyl)propane, also called o,p'-bisphenol-A; 2,2,4-trimethyl-4-(4-hydroxyphenyl)chroman, trihydroxyphenyl compounds, such as 4,4'-(4-hydroxy-m-phenylenedlisopropyiidene)diphenyl, polyphenols, isopropenylphenol and/or spiro biindanes.

The temperature in the adduct crystallizer used in step d) preferably is from 30 to 95° C., more preferably from 35 to 65° C. The pressure in the adduct crystallizer preferably is from 0.5 to 1.3 kPa, more preferably from 0.7 to 1.1 kPa. A crystalline adduct of phenol and bisphenol-A in a 1:1 molar ratio in a mother liquor is formed. To optimize the crystal quality and shape, crystallization is preferably carried out in the presence of water and/or acetone as taught in patent U.S. Pat. No. 5,723,688.

The purification process of the present invention comprises in its preferred embodiments various recycling steps as described herein. To maintain the concentration of the impurities below a certain level, it may be advisable to remove a portion of the material from the process. For example, a portion of the bisphenol-rich organic phase can be removed from the purification process before the remaining portion is combined with phenol.

In step e) of the process of the present invention the crystalline adduct of phenol and bisphenol-A is separated from the mother liquor. The crystalline adduct can be recovered by techniques known in the art, such as filtration or centrifugation, preferably at atmospheric pressure. The temperature in step e) generally is from 40 to 75° C., preferably from 45 to 65° C. The crystals are preferably washed, for example with phenol, a phenol-acetone mixture or water, most preferably with phenol alone, to remove mother liquor from the crystals. Preferably, from 0.1 to 1.5 parts, more preferably 0.3 to 1 parts of phenol are used, based on the weight of bisphenol-A/phenol adduct. The separation of the solid bisphenol-A/phenol adduct from the product mixture and the washing of the solid adduct is preferably carried out at a temperature of from 35 to 95° C., more preferably of from 38 to 60° C.

According to a preferred embodiment of the present invention at least a portion of mother liquor obtained in step e) is recycled to step d). Preferably at least 80 percent, more preferably at least 90 percent of mother liquor is recycled. According to another preferred embodiment of the present invention at least a portion of the phenol that has been preferably used for washing the crystalline adduct obtained in step e) is recycled to step d). Preferably at least 50 percent, more preferably at least 80 percent of the phenol is recycled to step d). The remaining portion of the mother liquor and/or of the phenol, if any, is preferably removed from the process and disposed of to control the level of impurities. Preferably, the mother liquor and/or the phenol to be recycled is subjected to a distillation step to remove water and optionally other volatile materials, such as acetone and/or or a portion of the phenol before the mother liquor and/or the phenol is recycled to step d). The distillation step is preferably carried out at a temperature of from 50 to 200° C., more preferably from 70 to 170° C. at an absolute pressure of from 0.15 to 1 bar, preferably from 0.25 to 0.5 bar.

To maintain the concentration of the impurities below a certain level, it may be advisable to remove a portion of the material from the process.

According to a more preferred embodiment, the process of the present invention comprises the additional step of f) optionally subjecting at least a portion of the mother liquor obtained in step e) to a distillation step to remove water, g) contacting mother liquor from which water has been removed with a catalyst for isomerizing isomers of bisphenol-A to bisphenol-A; and h) recycling the mother liquor treated in step g) to step d). Preferably at least 20 percent, more preferably at least 40 percent of the mother liquor is subjected to steps f) to h). The distillation step f) can be carried out as described above. An isomerization step as such wherein one or more isomers of bisphenol-A are isomerized to bisphenol-A by means of an isomerization catalyst is known in the art. U.S. Pat. Nos. 4,375,567; 4,825,010; 4,822,923 and 5,105,026 European Patent Applications Nos. 0 552 518 A1 and 0 630 878 describe an isomerization step and isomerization catalyst. The catalyst is preferably a cation exchange resin in acid form. More preferably, it is a strongly acidic cation-exchange resin having a sulfonic acid group, such as a sulfonated styrene/divinylbenzene copolymer, sulfonated crosslinked styrene polymer, phenol-formaldehyde-sulfonic acid resin or benzene-formaldehyde-sulfonic acid resin. The isomerization step g) is preferably carried out at a temperature of from 40 to 100° C., more preferably from 50 to 80° C. The mother liquor treated in step g) is recycled to step d).

Most preferably, at least a portion of the mother liquor and the phenol used to wash the crystals in the solid/liquid separation of step e) are combined to a recycle liquor, the recycle liquor is subjected to an optional, but preferred distillation step to remove water, then the recycle liquor is contacted with a catalyst for isomerizing isomers of bisphenol-A to bisphenol-A and subsequently the isomerized recycle liquor is recycled to step d). The steps can be carried out as described above.

The crystalline adduct of phenol and bisphenol-A obtained in step e) can be melted and phenol can be distilled off to recover bisphenol-A in a known manner. Recovered bisphenol-A is preferably recycled to step a) of the process of the present invention. Alternatively, it may be used in the production of other products such as epoxy resins. Advantageously, a least a portion of the distilled phenol is recycled to step d) of the process.

The process of the present invention is preferably conducted continuously although it can also be conducted in batches. According to the process of the present invention bisphenol-A of high purity at a high yield is obtained. Generally the purity of bisphenol-A is 99 percent or more, under optimized conditions even 99.5 percent or more. Generally the yield of the process of the present invention comprising steps a) to e) is at least 75 percent or more, preferably at least 80 percent or more and under optimized conditions even 90 percent or more, based on the weight of the crude bisphenol-A. Crystalline bisphenol-A having very large and firm crystals is obtained.

Preferred embodiments of the present invention are described with reference to the drawings. It is to be understood that the drawings are not to be construed as limiting the scope of the invention.

In the Figures the Reference Numbers Mean:
1: feed stream of molten crude bisphenol-A
2: feed stream of water
3: bisphenol-A crystallizer
4: first solid/liquid separator
5: storage device for bisphenol-A
6: liquid/liquid separation stage
7: water-rich phase
8: bisphenol-rich phase
9: phenol stream
10: recycle liquor
11: adduct crystallizer
12: second solid/liquid separator
13: isomerization reactor
14: isomerized recycle liquor
15: crystalline bisphenol-A/phenol adduct
16: first distillation device
17: water
18: second distillation device
19: bisphenol-A recycle stream Referring now to FIG. 1, a feed stream 1 of molten crude bisphenol-A and a feed stream 2 of water are continuously fed into a bisphenol-A crystallizer 3 wherein the crystallization of bisphenol-A is conducted as described in step a) above. Bisphenol-A crystals in liquid phase are obtained and fed into a first solid/liquid separator 4, such as a centrifuge, wherein crystalline bisphenol-A is separated from the liquid phase as described in step b) above. The crystalline bisphenol-A is removed from the first solid/liquid separator 4, preferably washed and dried (not shown) and collected in a storage device 5 for bisphenol-A. The liquid phase is fed from the first solid/liquid separator 4 into a liquid/liquid separation stage 6, which typically comprises a decantation and/or a distillation step, where the liquid phase is divided into a bisphenol-rich organic phase and a water-rich phase. The water-rich phase 7 is removed from the liquid/liquid separation stage 6. The bisphenol-rich phase 8 is combined with a phenol stream 9 and/or a phenol-containing isomerized recycle liquor 14 and is fed into an adduct crystallizer 11, such as a continuous adduct crystallizer where the mixture is cooled as described in step d) above. A crystalline adduct of phenol and bisphenol-A in a mother liquor is formed, usually in the form of a suspension. The suspension is passed to a second solid/liquid separator 12, such as an adduct centrifuge, wherein crystalline bisphenol-A/phenol adduct is separated from the mother liquor and washed with phenol (not shown) as described in step e) above. The crystalline bisphenol-A/phenol adduct 15 is removed from the solid/liquid separator 12. The mother liquor and phenol are combined to a recycle liquor 10 which is contacted with an isomerization catalyst 13 for isomerizing isomers of bisphenol-A to bisphenol-A as described in step g) above. After the isomerization step the isomerized recycle liquor 14 is recycled to the adduct crystallizer 11.

Figure 2:
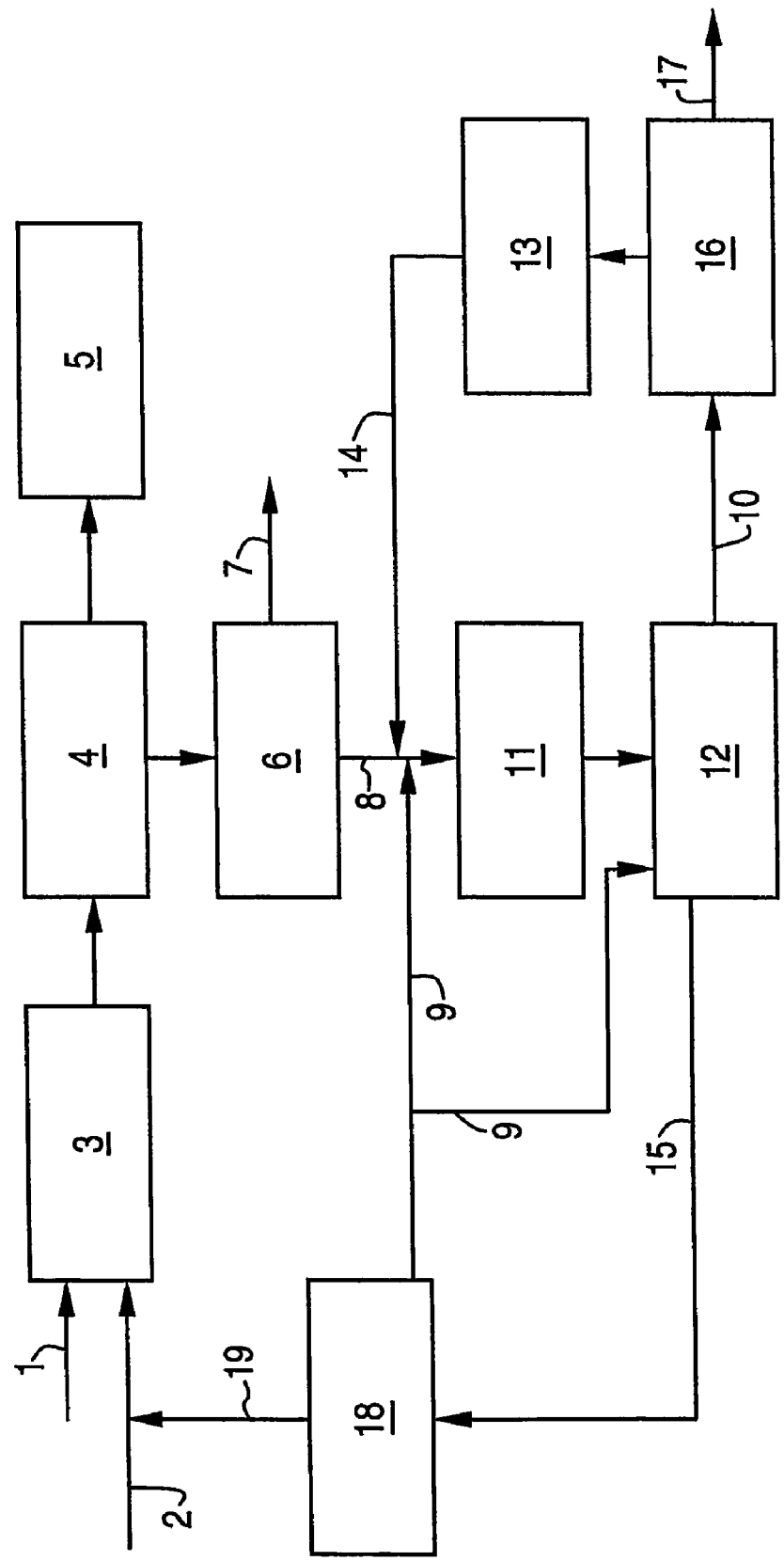
FIG. 2 represents a flow sheet of another preferred embodiment of the process of the present invention.

The embodiment of the present invention illustrated by FIG. 2 differs from the process illustrated by FIG. 1 in that the recycle liquor 10 is fed into a first distillation device 16 to distill off residuals amounts of water 17 before the recycle liquor is contacted in an isomerization reactor 13 with an isomerization catalyst. The crystalline bisphenol-A/phenol adduct 15 is fed to a second distillation device 18 wherein a phenol stream 9 is distilled off.

A portion of the phenol stream is sent to the second solid/liquid separator 12 for use as wash phenol and another portion of the phenol stream may be recycled to the adduct crystallizer 11. The bisphenol-A left in the second distillation device 18 is fed as a bisphenol-A recycle stream 19 to the bisphenol-A crystallizer 3 for further purification.

The present invention is further illustrated by the following example which should not be construed to limit the scope of the present invention. Unless otherwise indicated, all parts and percentages are by weight. All parts and percentages are average values measured over several days. The example illustrates the invention with reference to FIG. 2.

EXAMPLE

A feed stream 1 of 5840 kg/hr molten crude bisphenol-A containing 95.4 percent p,p'-bisphenol-A and other impurities of a temperature of 180° C. was combined with a feed stream 2 of 8700 kg/hr of water at a temperature of 100° C. under pressure sufficient to prevent partial vaporization of the water and fed to a bisphenol-A-crystallizer 3. The crystallizer 3 cooled the organic/water mixture to 95° C. by evaporative cooling. Purified bisphenol-A crystals in a liquid phase were formed. The bisphenol-A crystals were separated from the liquid phase and washed with hot water in a centrifuge 4, and were then dried and passed to a storage device 5 for bisphenol-A. The liquid phase from the centrifuge 4 was separated in a liquid/liquid separator 6 to obtain a water-rich phase 7 and a bisphenol-rich organic phase 8. 2030 kg/hr of the bisphenol-rich organic phase 8 were combined in a mix tank (not shown in FIG. 2) with 61370 kg/hour of recycle liquor 14. The isomerized recycle liquor 14 contained 80 percent phenol and 11.6 percent p,p'-bisphenol-A, the balance being impurities. The remaining 1300 kg/hr of the bisphenol-rich organic phase 8 was removed from the process. 63400 kg/hr of the produced mixture in the mix tank was fed to a continuous adduct crystallizer 11 operating at 50° C. The adduct crystals from the crystallizer were separated from the mother liquor and washed with phenol in an adduct centrifuge 12. The mother liquor and the phenol leaving the adduct centrifuge 12 were combined to a recycle liquor 10 and distilled in a first distillation device 16 to remove water and optionally other light impurities and then cooled to 75° C. 41400 kg/hr, of distilled recycle liquor 10 was fed to an isomerization reactor 13 which contained an isomerization catalyst and which was operated at 65° C. As the isomerization catalyst a sulfonated macroporous cross-linked polystyrene resin comprising 4 weight percent of divinylbenzene groups was used. The remaining distilled recycle liquor was combined with the isomerization reactor effluent and the bisphenol-A rich organic phase 8 from the liquid/liquid separator 6. The adduct crystals 15 recovered from the adduct centrifuge 12 were melted, stripped of a phenol stream 9 which was used to wash the adduct crystals in the adduct centrifuge 12. A bisphenol-A recycle stream 19 of 2070 kg/hr of molten recovered bisphenol containing 97.3 p,p'-bisphenol-A was combined with the feed stream 1 of 5840 kg/hr of molten crude bisphenol-A and the feed stream 2 of 8700 kg/hr of hot water and returned to the bisphenol-A crystallizer 3.

4500 kg/hr of purified bisphenol-A crystals were produced by this process. The product was analyzed and found to contain 99.6 percent p,p'-bisphenol-A and to have an alcohol color of 2.3 APHA.

What is claimed is:

1. A process for purifying bisphenol-A comprising the steps of
   a) cooling a liquid mixture comprising bisphenol-A and water in a bisphenol-A crystallizer to form bisphenol-A crystals in a liquid phase;
   b) separating the bisphenol-A crystals from the liquid phase;
   c) dividing at least a portion of the liquid phase into a bisphenol-rich organic phase and a water-rich phase;
   d) feeding phenol and at least a portion of the bisphenol-rich organic phase into an adduct crystallizer to form a crystalline adduct of phenol and bisphenol-A in a mother liquor; and
   e) separating the crystalline adduct from the mother liquor.

2. The process of claim 1 wherein at least a portion of the mother liquor obtained in step e) is recycled to step d).

3. The process of claim 2 wherein the mother liquor is subjected to a distillation step to remove water before the mother is recycled to step d).

4. The process of claim 1 comprising the additional steps of
   f) subjecting at least a portion of the mother liquor obtained in step e) to a distillation step to remove water;
   g) contacting mother liquor from which water has been removed with a catalyst for isomerizing isomers of bisphenol-A to bisphenol-A; and
   h) recycling at least a portion of the mother liquor treated in step g) to step d).

5. The process of claim 1 comprising the additional steps of
   g) contacting at least a portion of the mother liquor obtained in step e) with a catalyst for isomerizing isomers of bisphenol-A to bisphenol-A; and
   h) recycling at least a portion of the mother liquor treated in step g) to step d).

6. The process of claim 1 wherein the crystalline adduct obtained in step e) is washed with phenol.

7. The process of claim 6 wherein at least a portion of the phenol that has been used for washing the crystalline adduct is recycled to step d).

8. The process of claim 7 wherein at least a portion of the phenol that has been used for washing the crystalline adduct is first subjected to a distillation step to remove water and then recycled to step d).

9. The process of claim 6 wherein at least a portion of the phenol that has been used for washing the crystalline adduct and at least a portion of the mother liquor obtained in step e) are combined to a recycle liquor and recycled to step d).

10. The process of claim 9 wherein the recycle liquor is subjected to a distillation step to remove water before the recycle liquor is recycled to step d).

11. The process of claim 10 wherein after the distillation step the recycle liquor is contacted with a catalyst for isomerizing isomers of bisphenol-A to bisphenol-A before the recycle liquor is recycled to step d).

12. The process of claim 5 wherein the catalyst for isomerizing isomers of bisphenol-A to bisphenol-A is a cation exchange resin in acid form.

13. The process of claim 1 wherein the bisphenol-A crystals which have been separated from the liquid phase in step b) are melted, mixed with water, cooled in a second bisphenol-A crystallizer to form bisphenol-A crystals in a liquid phase and the crystals are separated from the liquid phase.

14. The process of claim 1 wherein crystalline adduct obtained in step d) is subjected to a distillation step to distill off phenol and the resulting bisphenol-A is recycled to step a).

15. The process of claim 11 wherein the catalyst for isomerizing isomers of bisphenol-A to bisphenol-A is a cation exchange resin in acid form.

16. The process of claim 5 wherein the bisphenol-A crystals which have been separated from the liquid phase in step b) are melted, mixed with water, cooled in a second bisphenol-A crystallizer to form bisphenol-A crystals in a liquid phase and the crystals are separated from the liquid phase.

17. The process of claim 11 wherein the bisphenol-A crystals which have been separated from the liquid phase in step b) are melted, mixed with water, cooled in a second bisphenol-A crystallizer to form bisphenol-A crystals in a liquid phase and the crystals are separated from the liquid phase.

18. The process of claim 5 wherein crystalline adduct obtained in step d) is subjected to a distillation step to distill off phenol and the resulting bisphenol-A is recycled to step a).

19. The process of claim 11 wherein crystalline adduct obtained in step d) is subjected to a distillation step to distill off phenol and the resulting bisphenol-A is recycled to step a).

* * * * *